US008834343B2

(12) United States Patent
Vodermayer et al.

(10) Patent No.: US 8,834,343 B2
(45) Date of Patent: Sep. 16, 2014

(54) HEART SUPPORT DEVICE

(75) Inventors: Bernhard Vodermayer, Gilching (DE); Harald Wagner, Seefeld (DE); Wolfgang Schiller, Bonn (DE); Thomas Schmid, Bernried (DE)

(73) Assignee: Deutsches Zentrum Fur Luft-Und, Cologne (DE)

( * ) Notice: Subject to any disclaimer, the term of this patent is extended or adjusted under 35 U.S.C. 154(b) by 363 days.

(21) Appl. No.: 12/936,323

(22) PCT Filed: Apr. 3, 2009

(86) PCT No.: PCT/EP2009/054027
§ 371 (c)(1),
(2), (4) Date: Jan. 13, 2011

(87) PCT Pub. No.: WO2009/121962
PCT Pub. Date: Oct. 8, 2009

(65) Prior Publication Data
US 2011/0137107 A1    Jun. 9, 2011

(30) Foreign Application Priority Data

Apr. 5, 2008   (DE) .......................... 10 2008 017 448

(51) Int. Cl.
*A61N 1/362*   (2006.01)
*A61M 1/12*    (2006.01)
*A61M 1/10*    (2006.01)

(52) U.S. Cl.
CPC ............... *A61M 1/106* (2013.01); *A61M 1/122* (2014.02); *A61M 1/1063* (2014.02)
USPC .................. 600/16; 600/17; 600/18; 623/3.1; 623/3.2; 623/3.3

(58) Field of Classification Search
CPC .... A61M 1/1063; A61M 1/106; A61M 1/122
USPC .................................. 600/16–18; 623/3.1–3.3
See application file for complete search history.

(56) References Cited

U.S. PATENT DOCUMENTS 3,568,214 A      3/1971  Goldschmied
4,957,477 A *    9/1990  Lundback ....................... 600/16
(Continued)

FOREIGN PATENT DOCUMENTS

EP    0247015    11/1987
FR    1458525    3/1966

OTHER PUBLICATIONS

International Search Report dated Sep. 1, 2009 for PCT/EP2009/054027.
(Continued)

*Primary Examiner* — Michael Kahelin
*Assistant Examiner* — Mallika D Fairchild
(74) *Attorney, Agent, or Firm* — Ohlandt, Greeley, Ruggiero & Perle, LLP

(57) ABSTRACT

A heart support device for pulsatile delivery of blood comprising a first and a second ventricle and a pump. Both ventricles comprises a fluid chamber and a blood-conveying chamber, wherein each fluid chamber can be filled with a fluid or emptied by way of the pump in such a way that an expansion or contraction of the fluid chamber occurs. In an expansion of the fluid chamber of a ventricle, a compression of the blood-conveying chamber of the same ventricle takes place, wherein a rigid pressure plate is disposed between a fluid chamber and the respective blood-conveying chamber, said pressure plate being able to move in the direction of the respective blood-conveying chamber.

12 Claims, 4 Drawing Sheets

(56) References Cited

U.S. PATENT DOCUMENTS

| | | | |
|---|---|---|---|
| 5,089,018 A | 2/1992 | Lapeyre et al. | 623/3 |
| 5,135,539 A | 8/1992 | Carpentier | 623/3 |
| 5,346,458 A | 9/1994 | Affeld | 600/16 |
| 2002/0147495 A1 | 10/2002 | Petroff | 623/3.25 |

OTHER PUBLICATIONS

International Preliminary Report dated Nov. 25, 2010 for PCT/EP2009/054027.

* cited by examiner

HEART SUPPORT DEVICE

BACKGROUND

1. Field of the Invention

The disclosure relates to a heart support device for pulsatile delivery of blood.

2. Discussion of the Background Art

Heart support devices, particularly mechanical systems for support of the blood circulation (VAD: Ventricular Assist Device) are implanted into the body of a patient suffering from cardiac insufficiency. Such devices will take over a part of the pumping work, thus stabilizing the blood circulation, e.g. until a donor organ has become available. Recent search has revealed that, during use of a heart support device, the cardiac function can improve to an extent favorable enough to allow for explanation of the system without subsequent heart transplantation.

Artificial heart pumps can be adapted to the most diverse requirements and, in contrast to donor hearts, are readily available without a waiting period. However, such heart support devices have to meet high demands with regard to the chosen technology and the tolerability of the implants. For instance, the blood may happen to be damaged by the pumping work. The power supply to the electrically operated systems, e.g. via cables passing through the abdominal wall, harbors a considerable risk of infection to the patient. Further, low degrees of efficiency will cause high energy consumption and will heat the surrounding tissue. Often, the assisted blood circulation has to be maintained through months or years. The systems are subjected to strong mechanical stresses. Since it is not possible to exchange blood pumps quickly, such pumps must have a very high failure safety.

DE 40 201 20 describes a heart support system which is operated hydraulically. A displacement pump is provided for pumping a hydraulic liquid alternately into a first and a second hydraulic chamber, the hydraulic liquid being separated by a flexible membrane from the blood-contained in the hydraulic chamber—that is to be conveyed. By filling the first hydraulic chamber with hydraulic liquid, the blood within the chamber will be displaced and, via a valve, be conveyed into the circulation. The hydraulic pump is arranged between the two hydraulic chambers and partially within the hydraulic chambers themselves.

A disadvantage of the above described device resides in that the two hydraulic chambers, having two blood chambers arranged laterally adjacent thereto, as well as the hydraulic pump located between the hydraulic chambers, together have a large construction height and thus can be implanted into a patient's body only with considerably difficulty.

It is an object of the disclosure to provide a heart support device having a low construction height.

SUMMARY

A heart support device for pulsatile delivery of blood comprises a first and a second ventricle as well as a pump. Each of said two ventricles comprises a fluid chamber and a blood-conveying chamber, each fluid chamber being able, with the aid of said pump, to be filled with a fluid or to be evacuated in a manner causing an expansion or contraction of the fluid chamber.

Preferably, no blood is included in the fluid chamber.

According to the disclosure, expansion of a fluid chamber of a ventricle will result in compression of the blood-conveying chamber of the same ventricle. In this manner, it is possible to convey blood into the blood circulation, while both the left and the right ventricle can be supported. A volume compensating reservoir compensating for the conveyed volume is not required.

According to the disclosure, said pump is arranged outside said first and second fluid chambers and/or outside said first and second ventricles.

Thereby, it is rendered possible to place or implant the pump and the two ventricles at different sites in or on a patient's body. Preferably, for this purpose, the pump can be connected to the fluid chambers via a fluid conduit of corresponding length. Thus, the device of the disclosure has a reduced construction height and can be implanted also into the body of smaller patients in a less problematic way.

Preferably, the first and the second ventricles are arranged adjacent to each other and, e.g., comprise a common partition wall. Particularly, the two ventricles can be located adjacent to each other while separated from each other exclusively by a partition wall.

By the design of the heart support device as provided by the disclosure, it is possible to arrange the pump at a distance from the two ventricles and/or the fluid chambers. Said distance can e.g. be larger than 10 cm and with particular preference larger than 15 cm. This offers the possibility to arrange the drive pump in an electronics housing, arranged separate from the heart pump, which also accommodates rechargeable batteries for operation of the pump as well as electronics for control. The resultant advantage lies in the minimizing of the volumes of the implanted components. This will enhance a full implantability of the components. Particularly, the pump can be arranged laterally next to the first and the second ventricle. Also an arrangement above or below the two ventricles is possible. Further, for instance, the two ventricles can be arranged at a lateral offset from each other on the left and right sides while preferably being directly adjacent to each other, i.e. abutting each other. In this case, the pump can be connected to the two ventricles via a fluid conduit and can be arranged, e.g., above the two ventricles, i.e. cranially relative to the ventricles. Thus, the pump is preferably not arranged between the first and the second ventricle and/or not between the first and the second fluid chamber.

The fluid conveyed by the pump preferably is a hydraulic fluid, wherein the fluid in the sense of the disclosure is not the blood of a patient. Instead, the fluid can be, e.g., a liquid causing the blood to be conveyed by corresponding contraction of the blood-conveying chambers.

According to a particularly preferred embodiment, said partition wall by which the two ventricles are separated from each other, is arranged stationary relative to the heart support device. This means that, when the fluid chamber is being expanded, the partition wall is not displaceable, so that an expansion of the fluid chamber will cause a compression of the blood-conveying chamber and will thus effect a delivery of blood into the blood stream.

Said partition wall is preferably made of the same material as the ventricles themselves. For instance, the two pump chambers and the partition wall can be produced in a sole manufacturing process and, at a later time, be easily integrated into an enclosing housing. The common wall, i.e. the partition wall, preferably has a thickness slightly larger than that of the ventricle walls so that its stiffness is increased. In spite of its larger thickness, the partition wall is preferably flexible. First, this flexibility will have the effect of a certain yieldingness during the pumping operation, thus allowing for the blood to be discharged in a gentle manner. Thereby, the pump can be used with little wear, and the useful life of the system can be increased. Second, thereby, a flow-optimized conveyance can be achieved in the pumping chambers. In addition to these benefits, the system can be given a still more compact design so that the blood conduits to and from the heart can be kept at minimum length. Thus, one can choose an implantation site close to the heart. In the presently described embodiment, said membrane is preferably elastic.

The fluid chambers can each be separated from the blood-conveying chambers by a flexible elastic membrane. This membrane is preferably of a two-layered design wherein, between the two layers of the membrane, a liquid-filled gap can be provided for reducing the friction between the two layers. The gap can be filled e.g. with silicone oil.

An independent disclosure relates again to a heart support device for pulsatile delivery of blood, comprising a first and a second ventricle and a pump. In correspondence to the disclosure as described above, the two ventricles comprise a respective fluid chamber and a respective blood-conveying chamber, wherein, with the aid of said pump, each fluid chamber can be filled with a fluid or be evacuated, thus causing an expansion or contraction of the fluid chamber. An expansion of the fluid chamber of a ventricle will result in a compression of the blood-conveying chamber of the same ventricle. An essential feature of the second disclosure resides in the provision of a respective, preferably stiff pressure plate arranged between a fluid chamber and the corresponding blood-conveying chamber, said pressure plate being displaceable in the direction toward the respective blood-conveying chamber.

In this arrangement, the fluid chamber can be formed as a bellows, squib or balloon. Via said pressure plate, an expansion of the fluid chamber will entail a compression of the respective blood-conveying chamber.

The pressure plate can have a surface larger in size than the base surface of the fluid chamber so that, in the fully expanded state of the fluid chamber, the volume of the fluid will be smaller than the volume of the conveyed blood. Thus, the use of a preferably stiff pressure plate makes it possible to deliver a larger blood volume with the aid of a smaller quantity of fluid. There will occur a translation of the pressure and of the volumes. The heart support device according to the second disclosure can comprise all features of the first disclosure. Particularly, a stationary and thickened partition wall can be provided between the two ventricles.

According to a preferred embodiment, the fluid chamber comprises stiff lateral walls which extend vertically to the pressure plate so as to prevent the lateral walls from yielding due to the applied pressure. The connection between said two lateral walls, i.e. the side of the fluid chamber facing in the direction of the pressure plate, can be flexible and stretchable.

For instance, the steps of said squib, when seen in sectional view, can form a lamellar structure which is able to expand under the influence of the fluid pressure and thus will press onto the pressure plate in the manner of a telescope.

Said squib can further be realized as a balloon which is ball-shaped and has a smaller volume than the blood chamber. The amount of the diameter of the balloon is only as large as the width of the blood chamber when viewed in lateral cross section.

The heart support devices according to the first disclosure and the second disclosure can further comprise the features described hereunder. There can be provided stiff housing walls, with the ventricles arranged therebetween. Further, the first and second blood-conveying chambers can be flexible and, particularly, stretchable.

According to a particularly preferred embodiment, the ventricles are of a stiff nature, with the fluid chambers being separated by an elastic membrane from the respective blood-conveying chamber of a stiff ventricle. Thus, the volume of the first and second blood-conveying chambers can be enlarged particularly by an underpressure in the respective fluid chamber and the resultant elastic deformation of the elastic membrane. With particular preference, the volume of the first and second blood-conveying chambers can be reduced, subsequent to its enlargement caused by said underpressure, by an inherent tension of the elastic membrane, particularly without using an overpressure in the respective fluid chamber.

Preferably, the shape of the stiff ventricle is selected to achieve an optimization of the flow. When using heart support devices, it is imperative to keep the ventricles free of regions with little or no movement of the blood because such occurrences would have a thrombogenic effect. It is thus important to achieve an optimized flow in the blood-conveying chamber and in the conduits. This can be realized in that the stiff ventricle is given a flow-optimizing shape, i.e. a shape which will enhance the blood flow. In this regard, it is of essence that the membrane separating the fluid chamber from the blood-conveying chamber is elastic so that, in the filled state of the blood-conveying chamber, the membrane will be in full abutment on the inner wall of the stiff ventricle and thus will have the flow-optimizing shape of the stiff ventricle. During discharge of the blood, the surface of the membrane will change due to the membrane's elasticity so that the membrane, once it has reached its relaxed state, will not present any kinking or warping which could have an adverse effect on the blood flow.

The above described embodiment can also be operated by hydraulic actuation wherein the blood-conveying chamber can be enlarged by an underpressure and the blood can be discharged again by an overpressure generated by a hydraulic liquid. For discharge of the blood, there can be additionally used the inherent tension of the elastic membrane.

Preferably, by use of said pump, the fluid chamber of the first ventricle and the fluid chamber of the second ventricle can be alternately filled with fluid and evacuated of fluid.

For replenishing fluid that has been diffused, a replenishment port can be provided which is accessible externally of the patient's body, e.g. via a syringe.

In each of the above described heart support devices, use can be made of electric pumps as known from the state of the art. Advantageously, the electric pumps should have a low construction height and a high running performance.

Preferred embodiments of the disclosure will be explained hereunder with reference to the Figures.

DETAILED DESCRIPTION OF THE PREFERRED EMBODIMENT

Figure 1:
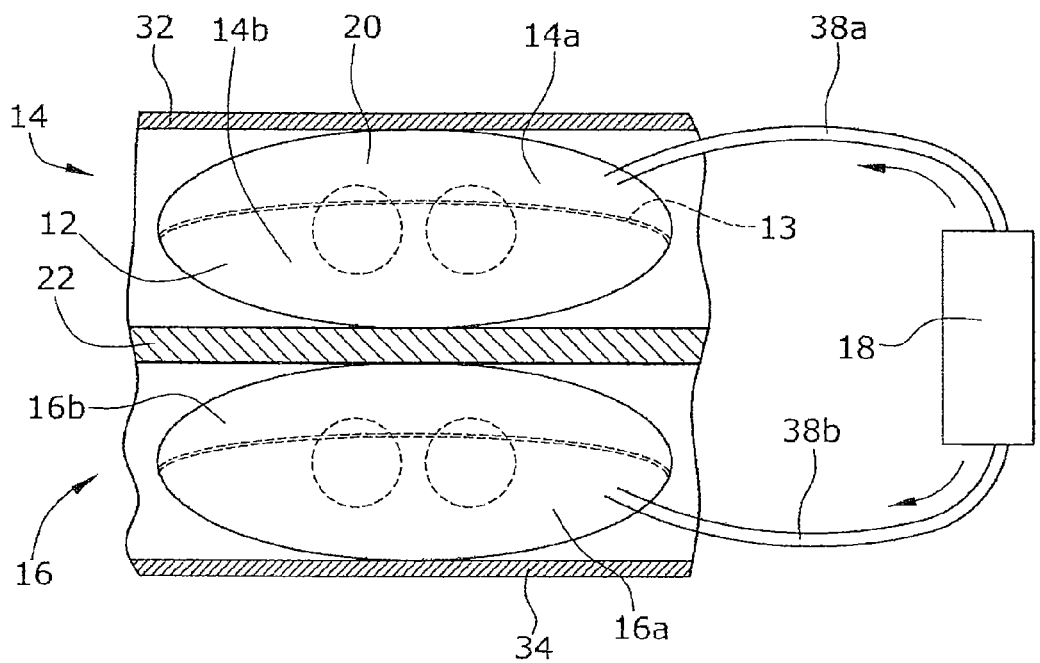
FIG. 1 is a schematic view of a first embodiment of the heart support device according to the first disclosure.

As shown in FIG. 1, a heart support device for pulsatile delivery of blood 12 comprises a first 14 and a second 16 ventricle. Each ventricle comprises a fluid chamber 14a,16a and a blood-conveying chamber 14b,16b. Said fluid chambers are filled with hydraulic liquid. Fluid chamber 14a is connected to a pump 18 via a fluid conduit 38a. Fluid chamber 16a is connected to pump 18 via a fluid conduit 38b. By means of pump 18, hydraulic liquid will be pumped alternately into said first and second fluid chambers 14a,16a, causing an alternate expansion of the two fluid chambers 14a,16a. Expansion of fluid chamber 14a of ventricle 14 will result in compression of blood-conveying chamber 14b of the same ventricle 14. The same applies to the second ventricle 16.

Pump 18 is arranged outside the first and second ventricles 14,16 as well as outside the first and second fluid chambers 14a,16a. As can be seen in FIG. 1, pump 18 is arranged, e.g., on the right-hand side of the two ventricles 14,16. Thus, the pump is located at a lateral offset from the ventricles 14, 16. However, the ventricles 14,16, instead of being arranged above each other as depicted in FIG. 1, can also be disposed laterally of each other in the body of a patient so that pump 18 can be located e.g. above or below the ventricles 14,16.

According to FIG. 1, the two ventricles 14,16 are arranged adjacent to each other and are separated from each other by a stationary partition wall 22. The heart support device is delimited by a first and a second housing wall 32,34.

The fluid chamber 14a,16a and the blood-conveying chamber 14b,16b are separated from each other by a respective double-layered membrane 13.

Figure 2:
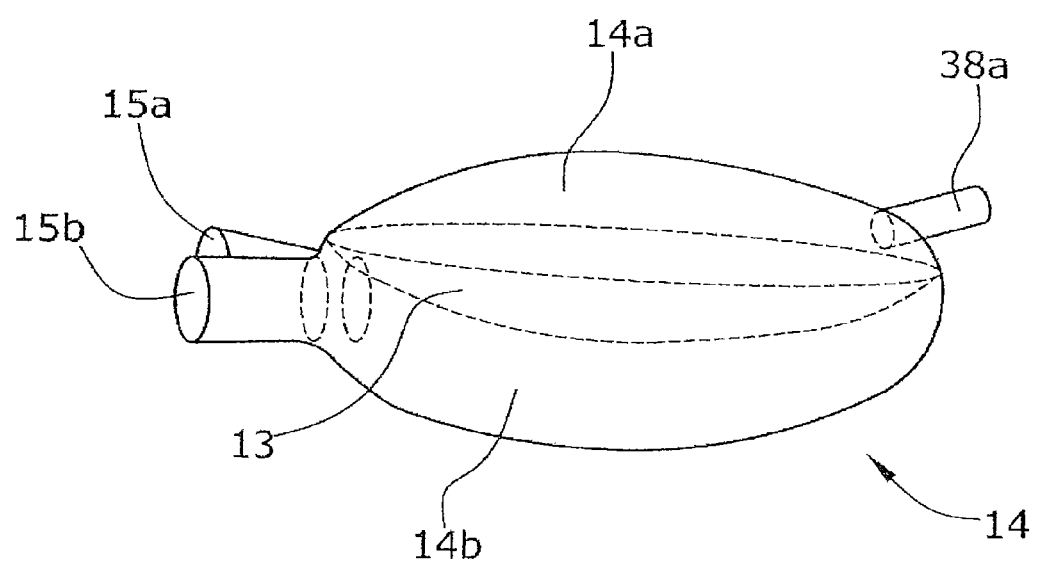
FIG. 2 is a schematic view of the first ventricle of the embodiment according to FIG. 1, FIGS. 3a and 3b are schematic views of an embodiment of the heart support device according to the second disclosure.

FIG. 2 is a lateral view of the first ventricle 14 of FIG. 1. The blood-conveying chamber 14b comprises a blood inlet conduit 15a and a blood outlet conduit 15b, which conduits will be connected to blood vessels of the patient during the implantation process of the heart support device. Said conduits 15a,15b can include valves for control of the blood flow.

Figure 3A:
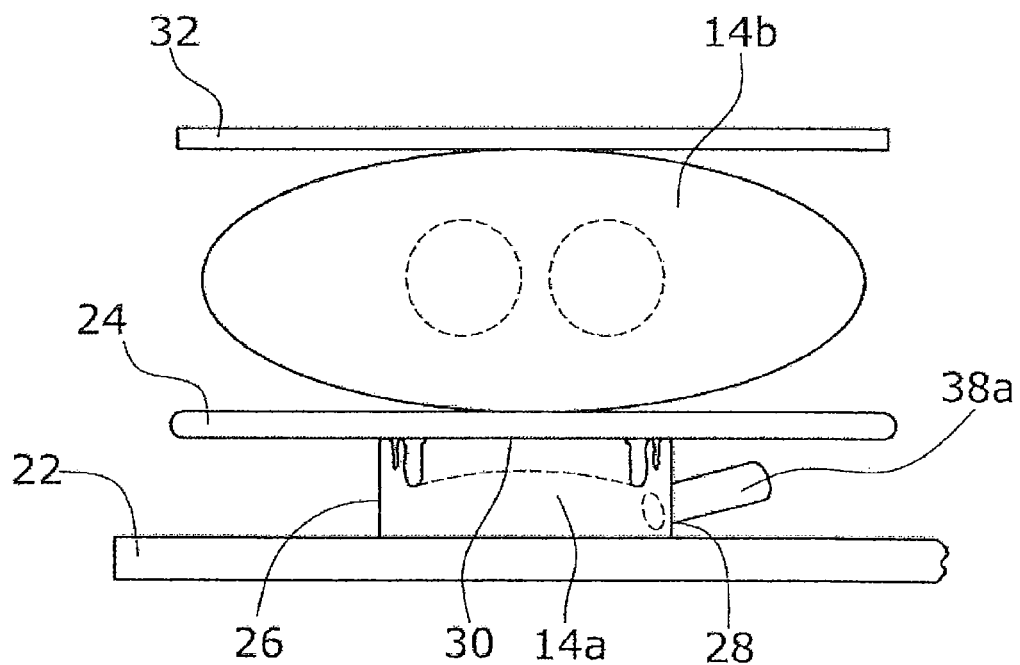
Figure 3B:
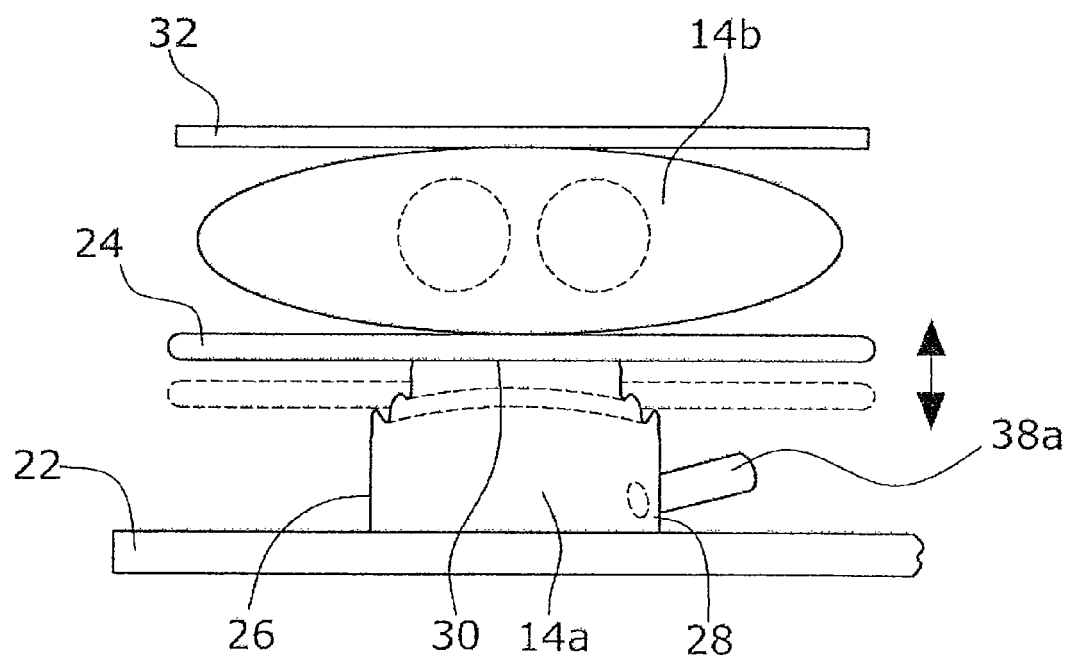

According to a second disclosure shown in FIGS. 3a and 3b, a stiff pressure plate 24, adapted to be displaced in the direction of the respective blood-conveying chamber 14b, 16b, is arranged between each fluid chamber 14a, 16a and the respective blood-conveying chamber 14b,16b. In FIGS. 3a and 3b, only the first ventricle 14 is illustrated, the second ventricle 16 being arranged below the partition wall 22 of the housing in mirror image to the first ventricle 14.

Figure 5:
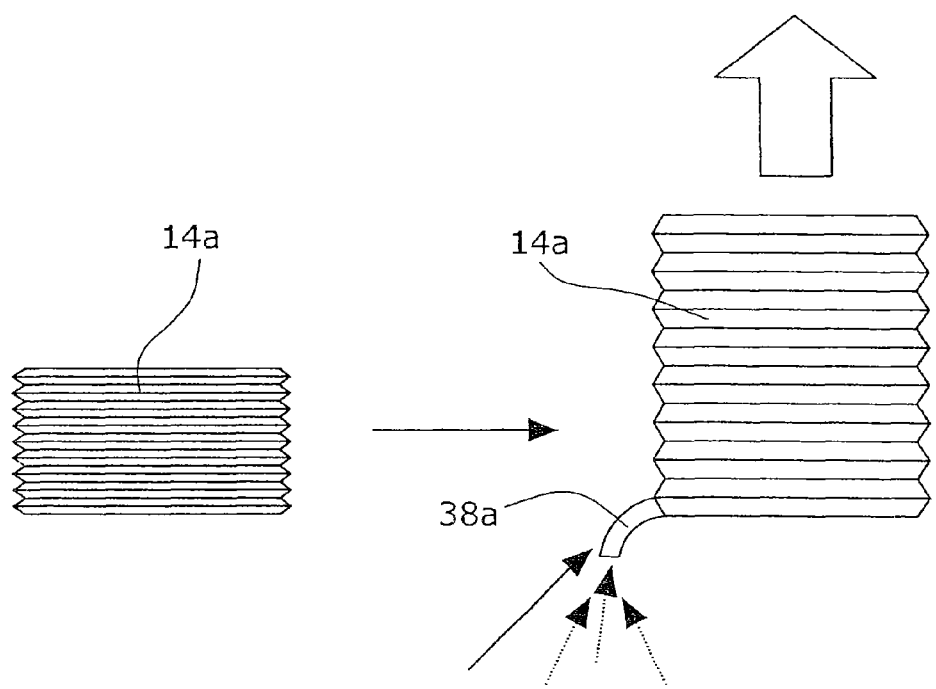
FIG. 5 is a schematic view of a squib.

In the illustrated embodiment, fluid chamber 14a is formed as a squib. According to FIG. 5, said squib, comprising a base surface of any desired shape, can be designed in the manner of an accordion or a bellows. The folds are made of a material with tensile strength so as to allow for stretching only in the direction of the longitudinal axis of the squib. Stretching in the other two directions, however, is prevented. In the non-expanded state, the squib is flat while, on the other hand, its base surface is not significantly enlarged. Via said hydraulic line 38a, which is arranged laterally of squib 14a near the base surface of the latter, pressurized air or a hydraulic fluid can be supplied. When the squib is expanded, a force F can be exerted on the target object. Squib 14a is connected to pump 18 via hydraulic line 38a, wherein a delivery of hydraulic liquid into squib 14a will cause the squib to expand. Thereby, the stiff pressure plate 24 will be pressed into the direction of blood-conveying chamber 14, with resultant compression of blood-conveying chamber 14b. Since squib 14a has a base surface which is smaller than the surface of pressure plate 24, the volume of the hydraulic liquid 20 required for expansion of squib 14a is smaller than the volume of the conveyed blood 12. Pressure plate 24 can also be integrated into the distal end of squib 14a. On the left side of FIG. 5, a non-expanded squib 14a is shown, while an expanded squib 14a is shown on the right side.

It is preferred that the squib 14a is formed as non-segmented component, i.e. in one piece, thus preventing the occurrence of leakage problems. Further, in comparison to an actuator consisting of several segments, friction losses at the segment contact regions which may cause a reduction of the mechanical efficiency of the pump, can be reduced. Preferably, the squib 14a does not need bearings, seals, tractive connections or the like for establishing a safe and reliable operation. When using a squib in the embodiments of the disclosure, the pressure plate 24 may be omitted so that the side or wall of squib 14a facing toward the blood-conveying chamber 14b will press directly onto the blood-conveying chamber 14b. Thus, squib 14a can be formed as a part of blood-conveying chamber 14b.

Further, the squib can be designed in such a manner that its sectional surface corresponds to the projection surface of the blood-conveying chamber or the membrane. Thereby, the force will be equally distributed onto the blood-conveying chamber, and the device can be realized with a low construction height. Also in case of this design, it is not necessary to provide a separate pressure plate. Preferably, the common wall between the squib and the blood-conveying chamber or the membrane has a suitable shape or surface for enhancing the blood flow.

The side walls 26,28 of squib 14a extend vertically to pressure plate 24 and are of a stiff nature, thus allowing an expansion of squib 14a to occur only in the direction of blood-conveying chamber 14b. The side 30 of fluid chamber 14a facing in the direction of pressure plate 24 and facing also in the direction of the blood-conveying chamber 14b, is flexible and stretchable.

In FIG. 3b, a blood-conveying chamber 14b is shown in its compressed state.

Figure 4A:
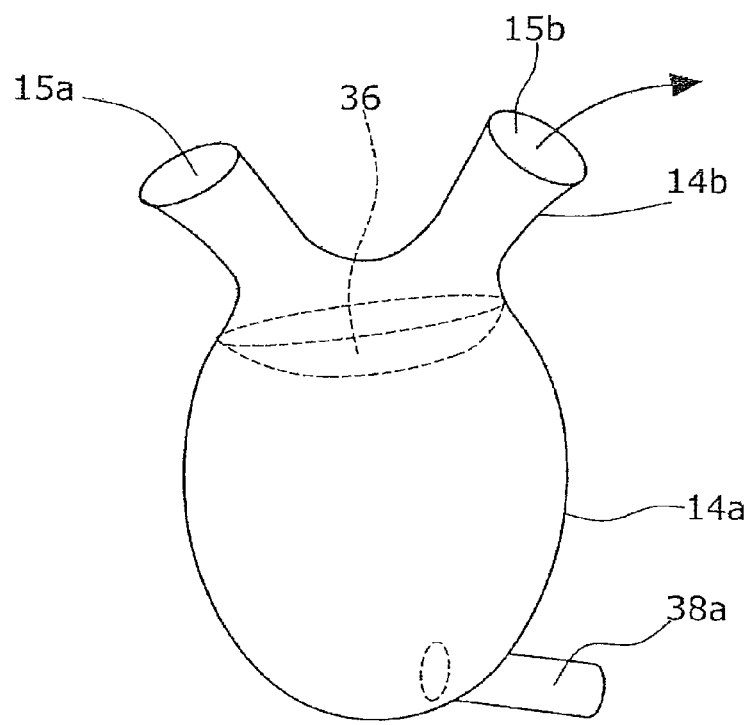
FIGS. 4a and 4b are schematic views of a further embodiment of the heart support device according to the first disclosure.
Figure 4B:
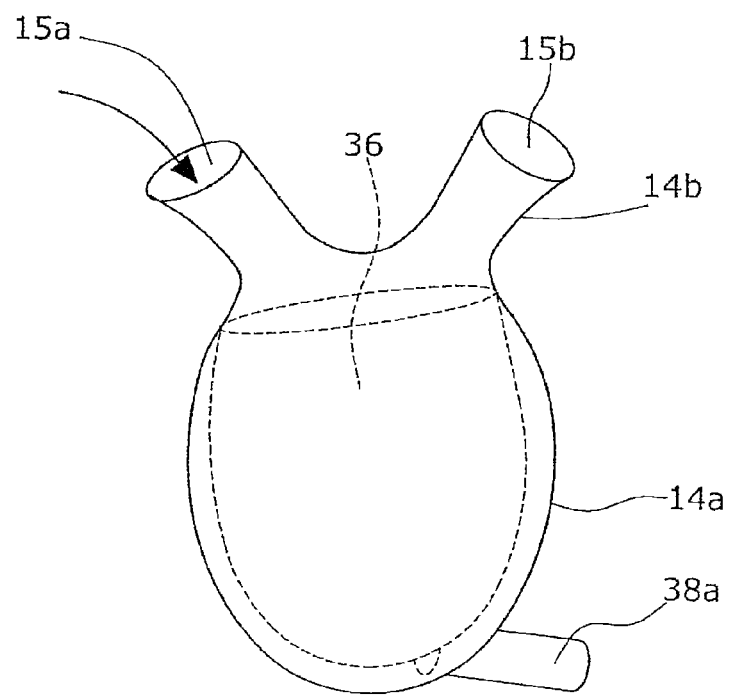

A further embodiment of the heart support device of the disclosure is shown in FIGS. 4a and 4b. Illustrated in these Figures is only one ventricle 14, which is of a stiff nature. A elastic membrane 36, preferably bonded to the inner wall of ventricle 14, separates the fluid chamber 14a from the blood-conveying chamber 14b of the stiff ventricle 14. The volume of blood-conveying chamber 14b can be enlarged by an underpressure in fluid chamber 14a in that the elastic membrane will be elastically deformed (see FIG. 4). For generating an underpressure in fluid chamber 14a, the fluid will be pumped out from the stiff ventricle 14 via fluid conduit 38a, with the effect that the pressure in blood-conveying chamber 14b will be higher than the pressure in fluid chamber 14a. In this state, according to FIG. 4b, blood is supplied via blood inlet conduit 15a into blood-conveying chamber 14b. Subsequent to the enlargement of the volume of blood-conveying chamber 14b caused by the underpressure, the volume will be reduced again. This takes place due to the inherent tension of the elastic membrane 36, so that the blood will be pressed out of blood-conveying chamber 14b via blood outlet conduit 15b.

In order to avoid dead zones in blood-conveying chamber 14b, it is important, apart from a flow-enhancing shape of the stiff ventricle 14, to find a suitable site where the elastic membrane 36 is connected to the inner wall of the ventricle 14. The surrounding connecting line on which the membrane 36 is connected to the inner wall of ventricle 14, is arranged in such a manner within ventricle 14 that no dead zones will develop within blood-conveying chamber 14b. Thus, for instance, the elastic membrane 36 can be connected to the inner wall at the narrowest site of ventricle 14. Preferably, the connection site is selected in such a manner that, in the filled state of blood-conveying chamber 14b, the elastic membrane 36 extends tangentially to the outer wall of blood inlet conduit 15a. The same applies to blood outlet conduit 15b. Since the stiff ventricle 14 is formed with a constriction below the inlet and outlet lines 15a,15b, it is particularly preferred that the membrane 36 is connected to ventricle 14 at the apex of said constriction, i.e. at the narrowest site of ventricle 14, thus preventing a development of dead zones in the blood-conveying chamber above or below this connecting line. Preferably, the ventricle 14 is designed for flow-enhancement by having no undercuts and particularly by having a round uniform shape.

The invention claimed is:

1. A heart support device for pulsatile delivery of blood, comprising:
    a first and a second ventricle, and
    a pump,
        each of said two ventricles comprising a respective fluid chamber and a respective blood-conveying chamber, and each fluid chamber being adapted, with the aid of said pump, to be filled with a fluid or to be evacuated in a manner causing an expansion or contraction of the fluid chamber,
        an expansion of the fluid chamber of the ventricle resulting in a compression of the blood-conveying chamber of the same ventricle, wherein
        between the fluid chamber and the corresponding blood-conveying chamber, a respective stiff pressure plate is arranged, said pressure plate being displaceable in the direction toward the respective blood-conveying chamber, and
        upon expansion of the fluid chamber, a compression of the respective blood-conveying chamber is effected via said pressure plate, wherein said fluid chamber has a base surface which is smaller than a surface of said rigid pressure plate so that, upon expansion of said fluid chamber, a volume of the fluid is smaller than a volume of the conveyed blood.

2. The heart support device according to claim 1, wherein said fluid chamber is provided in the form of a bellows, squib or balloon.

3. The heart support device according to claim 1, wherein the fluid chamber comprises stiff side walls extending vertically to the pressure plate.

4. The heart support device according to claim 3, wherein the fluid chamber has a side facing toward the pressure plate that is flexible and stretchable.

5. The heart support device according to claim 1, further comprising stiff housing walls, with the ventricles arranged between said housing walls.

6. The heart support device according to claim 1, wherein the blood-conveying chambers are flexible and stretchable.

7. The heart support device according to claim 1, wherein, by use of said pump, the fluid chamber of the first ventricle and the fluid chamber of the second ventricle can be alternately filled with fluid and evacuated of fluid.

8. The heart support device according to claim 1, further comprising a replenishment port for replenishing fluid that has been diffused.

9. A heart support device for pulsatile delivery of blood, comprising:
    a pump;
    a stiff outer housing divided into a first partition and a second partition by a stiff partition wall; and
    a first ventricle in said first partition, said first ventricle having a first fluid chamber, a first blood-conveying chamber, and a first stiff pressure plate between said first fluid and blood conveying chambers, said first fluid chamber being in fluid communication with said pump so as to be selectively filled or evacuated by said pump to cause an expansion or contraction of said first fluid chamber, wherein said expansion of said first fluid chamber within said first partition results in displacement of said first stiff pressure plate, due to constriction of said first ventricle in said first rigid partition, toward said first blood-conveying chamber to compress said first blood-conveying chamber; and
    a second ventricle in said second partition, said second ventricle having a second fluid chamber, a second blood-conveying chamber, and a second stiff pressure plate between said second fluid and blood conveying chambers, said second fluid chamber being in fluid communication with said pump so as to be selectively filled or evacuated by said pump to cause an expansion or contraction of said second fluid chamber, wherein said expansion of said second fluid chamber within said second partition results in displacement of said second stiff pressure plate, due to constriction of said second ventricle in said second rigid partition, toward said second blood-conveying chamber to compress said second blood-conveying chamber.

10. The heart support device according to claim 9, wherein said first and second fluid chambers are provided in the form of a bellows, squib or balloon.

11. The heart support device according to claim 9, wherein the first and second blood-conveying chambers are flexible and stretchable.

12. The heart support device according to claim 9, wherein said pump is configured to alternately fill and evacuate said first and second fluid chambers.

* * * * *